United States Patent [19]

Lonardo et al.

[11] Patent Number: 5,076,264
[45] Date of Patent: Dec. 31, 1991

[54] MEDICAL APPLIANCE FOR TREATING SPINAL CONDITIONS

[76] Inventors: John S. Lonardo, 7360 137 Street N., Seminole, Fla. 34646; Chris Lonardo, 5736 Baylake Dr. S., St. Petersburg, Fla. 33708

[21] Appl. No.: 706,483

[22] Filed: May 28, 1991

[51] Int. Cl.⁵ ............................ A61F 5/02; A61F 5/37
[52] U.S. Cl. ................................. 128/78; 128/874; 128/876
[58] Field of Search ............... 128/869, 78, 870, 873, 128/874, 875, 84 R, 87 C; 297/219, 410, 467, 188, 466, 485, 229, 464, DIG. 1, DIG. 2; 5/432, 436

[56] References Cited

U.S. PATENT DOCUMENTS

| | | | |
|---|---|---|---|
| 1,934,615 | 11/1933 | Selverstone | 297/188 |
| 2,267,103 | 12/1941 | Ireland | 297/485 |
| 4,559,933 | 12/1985 | Batard | 128/78 |
| 4,568,125 | 2/1986 | Sckolnik | 297/467 |
| 4,750,478 | 6/1988 | Bergeron | 128/78 |
| 4,789,202 | 12/1988 | Alter | 128/78 |
| 4,854,638 | 8/1989 | Marcus | 297/464 |
| 4,874,203 | 10/1989 | Henley | 297/464 |
| 4,912,788 | 4/1990 | Lonardo | 5/436 |

FOREIGN PATENT DOCUMENTS 2556587 6/1985 France .................. 297/464

Primary Examiner—Robert A. Hafer
Assistant Examiner—Michael Brown
Attorney, Agent, or Firm—Joseph C. Mason, Jr.; Ronald E. Smith

[57] ABSTRACT

A medical appliance, having a thick foam core received within a cover made of fleece, for simultaneously treating spinal, shoulder girdle, head, neck and related conditions. The appliance includes a seat cushion surrounded on three sides by a three-sided vest having a back wall and a pair of forwardly extending side walls. Each side wall includes an inwardly projecting protuberance formed on its inner surface that bears against the patient's waistline for therapeutic purposes when a belt that circumscribes the back and side walls is tightened, and a similar protuberance is formed in each side wall at the bottom thereof to help center the patient's hips atop the cushion and to hold them against lateral displacement. The rigidity of a side wall is enhanced by selectively placing a rigid stay member in a slot formed in each side wall. A head rest is adjustably mounted in a pocket secured to the exterior side of the back wall, and the length of straps interconnecting the back wall and the head rest are adjustable to control the position of a patient's head. Armrests and armrest extensions are provided on the exterior side of each side wall, and each armrest defines an overhang that is supported by the arm of a chair that supports the entire apparatus. The core and cover construction further allows the addition of sundry bolster pads to tailor the device to the needs of a patient.

20 Claims, 6 Drawing Sheets

MEDICAL APPLIANCE FOR TREATING SPINAL CONDITIONS

TECHNICAL FIELD

This invention relates, generally, to medical appliances. More particularly, it relates to a medical appliance having utility in the treatment of deformities, abnormalities, or misalignments in a patient's spinal and shoulder girdle area.

BACKGROUND ART

Spinal misalignments and related problems may be caused by poor bedding, improperly designed chairs, and the like. In most cases, the abnormality is easily corrected while still in its postural stage; correction becomes a little more problematic if the misalignment goes untreated and enters the structural stage.

Therapists have long relied upon appliances to help correct both postural and structural deformities. The appliance applies pressure at specific locations on the patient's body to gently urge the spine to return to its normal configuration.

The appliance may take the form of a seat cushion because a well-designed seat cushion positions the patient's body so that it is properly anchored; this anchoring provides a base that helps the rest of the spine to straighten.

Alternatively, the appliance may take the form of a corset or vest; appliances of that type wrap around the patient's trunk and gently persuade the spine to correct its alignment.

For example, a lumbar-sacral corset is shown in U.S. Pat. No. 4,559,933 to Batard. It includes the use of foam padding and hook and loop-type fastening members to facilitate its adjustment.

A seat cushion having utility in this field is shown in U.S. Pat. No. 4,912,788 to Lonardo; it is particularly adapted to anchor a patient's pelvic region while preventing the formation of decubitus ulcers.

Other earlier disclosures of interest include U.S. Pat. No. 3,362,402 to Loeffel et. al., and German patent No. 2,132,146.

The appliances heretofore known have utility and represented advances in the art at the time of their invention. However, none of the devices heretofore known can adequately treat the entire panoply of spinal and related deformities and misalignments. The known appliances do not fit people of differing body sizes, do not fit the exact contour of a chair that supports the appliance, cause patient discomfort because heat is trapped within the appliance, and are not easily adjustable to facilitate treatment of all conditions. The devices heretofore known also lack adequate means for maintaining the patient's head and neck in a therapeutic position and for abducting the patient's shoulders.

Moreover, the devices heretofore known lack means for properly positioning and comfortably anchoring the patient's pelvic and hip regions and for simultaneously properly and comfortably positioning, in a single device or framework, the patient's trunk region, head, neck, or shoulder girdle including the arms, hands, elbows, and forearms as needed.

The seat cushions of the prior art are not attachable to the corsets of the prior art and the head rests of the prior art are not attachable to the corsets. Accordingly, the seat cushions, corsets, and head rests heretofore known are not advantageously usable together. Just as importantly, the corsets and head rests of the prior art lack adequate means for adapting them to meet the specific requirements of individual patients. Adaptability is all-important in this field because no two people are exactly alike in body size and structure and no two people share the precise spinal deformity.

Thus, there is a need for a medical appliance that combines the best features of the prior art seat cushions, corsets, and head rests and that improves the corsets and head rests by being made fully adaptable to patients of all different sizes and spinal, shoulder, hand and arm conditions. Further improvement in devices for supporting patient's hands is also needed. In a broader sense, what is needed is a device that not only treats the spine and pelvic regions, but which gives full consideration to the entire upper trunk as well, including the upper extremities and the cervical spine.

There is a further need for a device that is easy to use and comfortable to the patient as well, but the prior art, when considered as a whole in accordance with the requirements of law, neither teaches nor suggests to those of ordinary skill in the art how the needed medical appliance could be provided.

DISCLOSURE OF INVENTION

The longstanding but heretofore unfulfilled need for a versatile sacral-lumbar vest that includes an adjustable head rest and means for treating a patient's arms and hands as well is now fulfilled. The novel device improves prior art seat cushions by providing means for detachably securing them to sacral-lumbar vests. The invention further includes a vest that contains features that enable it to be easily fit onto any patient and onto any chair having side arms and to treat any spinal, shoulder and upper extremity condition. The device further includes a novel head rest that enables the therapist to gradually bring a patient's head into proper alignment with the spine, and a novel hand splint that aligns and supports the hand to help overcome hand deformities.

Since the prior art seat cushions are fully described in the above-referenced patents, the present disclosure is directed primarily to the novel vest and the novel head, arm and hand rests that form a part thereof.

The vest member of the novel appliance is detachably securable, through the use of hook and loop-type fasteners, to any prior art seat cushion. The vest member includes a flat, transversely disposed, upstanding back wall and a pair of longitudinally disposed, upstanding side walls integrally formed therewith or fixedly secured thereto that project forwardly from opposite ends of the back wall. The back and side walls are specifically contoured to fit the configurations of chairs that support the appliance and to fit the human body. The side walls have cut away, dished upper edges to accommodate the patient's underarm area and the thickness of the side walls serves to abduct the patient's shoulders in a therapeutic manner. The back and side walls are made of a thick, open-celled foam or other suitable material and are covered by a thick cover made of fleece, Kodell brand synthetic fleece, or other fleece-like material that breathes well and that, accordingly, does not trap the patient's body heat when the patient is fitted with the appliance. The cover opens at its bottom edge and complemental hock and loop type fastener strips are affixed to opposing flaps thereof to facilitate easy opening and closing of the cover and hence facile insertion and removal of the back and side walls into and from the cover, respectively. The appliance also includes bolster pads that can be inserted where needed, and the foam and cover construction of the appliance facilitates the introduction or removal of said bolster pad or pads as needed.

Each side wall is specifically contoured to provide patient comfort and to enhance the utility of the device to the therapist. More particularly, the thickness and dished contour of the upper edges of the side walls therapeutically supports the patient's arms in the armpit area and provides abduction and extension of the shoulders and arms in proper anatomical alignment.

The outer surface of each side wall has an integrally formed, longitudinally extending arm rest formed therein, each arm rest has a concavity formed thereatop to accommodate a patient's arm and forearm, each armrest includes an adjustable length loop to maintain the patient's forearm in the concavity, and each armrest includes a telescoping extension member so that said armrest accommodates forearms of all lengths. The extension member includes a hand rest or splint as well, and the hand rest is designed in modular form so that hand rests of differing configurations can be attached to the extension member in response to the needs of differing patients.

Each armrest overlies the armrests of a chair when the appliance is positioned atop a chair. Significantly, the appliance has utility in connection with chairs of all types, including regular side arm chairs, wheelchairs and Gerichairs.

Each side wall further includes a longitudinally extending protuberance formed on its inner side; the protuberances may be brought to bear against the patient's waist line as needed by the therapist by tightening a pair of opposed straps each of which is fixedly secured to an associated side wall leading edge. Each side wall further includes another pair of protuberances at its lowermost end; said lower protuberances help to position the patient's hips in the center of the seat cushion. The therapeutic effectiveness of the side walls and protuberances formed therein depend in part upon the firmness of the arm rest of the chair that supports the appliance; this firmness helps anchor the patient's shoulders and arms in their respective elevated positions.

When the patient is properly seated atop the cushion and is strapped into the vest, the vest is affixed to the body and is sandwiched between the body and chair, thereby preventing shifting or other desired movement of the body.

The side walls and back wall of the vest and hence the protuberances are further tightenable around the trunk of the patient as needed by adjusting the length of a belt member that circumscribes the vest and which is held in place near the upper periphery thereof by a plurality of circumferentially spaced apart loop members. In a second embodiment, the belt loops are eliminated and the belt is replaced by a pair of strap members, each of said strap members having a first end fixedly secured to a front edge of a side wall and a second, hook and loop-covered free end for releasable engagement with its counterpart strap member. The strap members of the second embodiment perform the same vest-tightening function as the circumscribing belt member of the first embodiment, i.e., they serve to mold the vest into a precise fit about the patient's body.

Further structural features include a head rest that is slidably and adjustably received within a pocket member mounted to the back wall of the vest, a lap strap member that performs the function its name implies, i.e., that locks the patient in place and prevents lateral shifting, bolster pads for further tailoring the device to specific patient needs, e.g., for correcting and over-correcting spinal curvatures, a rigid stay member for enhancing the rigidity of a preselected vest side wall to thereby provide additional tension for spinal correction and control, razor lines to facilitate shortening of the vest height so that it can accommodate children or adults of shorter than average stature, additional razor lines for reducing the width of the vest as needed, and a strap for securing the entire assembly to a wheelchair or other support structure.

The novel head rest assembly includes a first pair of laterally spaced straps anchored at a first or lower end thereof to the back wall of the appliance, and the respective free upper ends thereof are detachably securable to opposite ends of the head rest base in an infinite plurality of positions of adjustment, thereby controlling the position of the head rest base and hence the position of the neck and head of the patient. A contoured, padded head-cradling member is detachably secured to the head rest base by hook and loop fastening means so that the position of the padded member can be adjusted relative to the base. A second pair of straps are mounted to opposite ends of the padded member and said straps retain the head of the patient against the padded member.

The primary, object of this invention is to provide the world's first combined vest, seat, head, arm, hand, and shoulder device for correcting spinal and shoulder girdle abnormalities.

A more specific object is to provide a vest having strategically placed protuberances and means for tightening those protuberances to urge the spine to straighten itself and to disallow abnormal deviations.

Yet another object is to provide a medical appliance of the type that fits onto a chair and that abducts the arms and shoulders of a patient treated by said appliance.

Still another object is to provide a vest and attached head rest that fits patients and side arm chairs of all sizes.

Another important object is to provide a novel head rest and unique means for adjusting the position of the head rest to further provide therapy to a patient undergoing treatment.

Another object is to provide adjustable and modular hand splints.

These and many other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

Similar reference numerals refer to similar parts throughout the several views of the drawings.

BEST MODES FOR CARRYING OUT THE INVENTION

Figure 1:
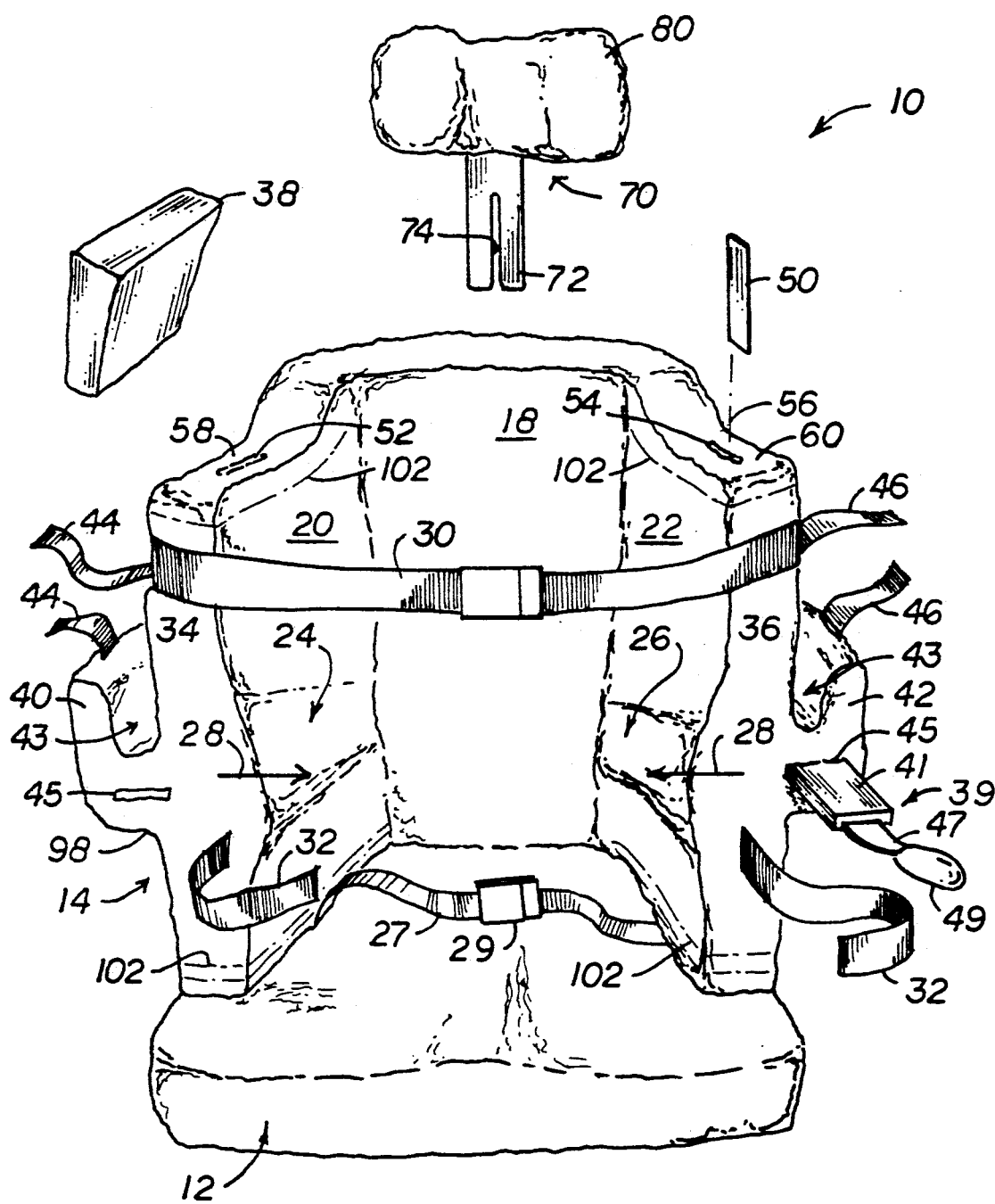
FIG. 1 is a frontal perspective view of a first exemplary embodiment of the novel apparatus.

Referring now to FIG. 1, it will there be seen that a first illustrative embodiment of the present invention is denoted as a whole by the reference numeral 10.

Sacral vest 10 includes three primary parts: seat cushion 12, vest member 14, and head rest assembly 70. There is no need here to repeat a detailed description of seat cushion 12, because the novel assembly has utility in connection with any suitable seat cushion of the prior art. However, it is important to note that vest 14 is detachably secured to cushion 12 by straps 16 (FIG. 2.) which are provided in spaced relation to one another about three sides (left, rear and right) of the lower periphery of vest 14. The straps 16 are provided with hook and loop-type fastening members and seat cushion 12 is provided with complemental hook and loop-type fasteners strips 13 to facilitate the attachment and detachment of the vest and cushion. Straps 16 may be secured to either the cushion 12 or the vest 14, although the straps are preferably anchored to vest 14. It should be understood from FIG. 2 that in this particular illustrative embodiment, there are a total of six straps 16 and mating strips 13.

Vest 14 includes an upstanding, transversely disposed back wall 18 and forwardly projecting, longitudinally disposed side walls 20, 22 that may be integrally formed therewith or formed separately therefrom.

Figure 5:
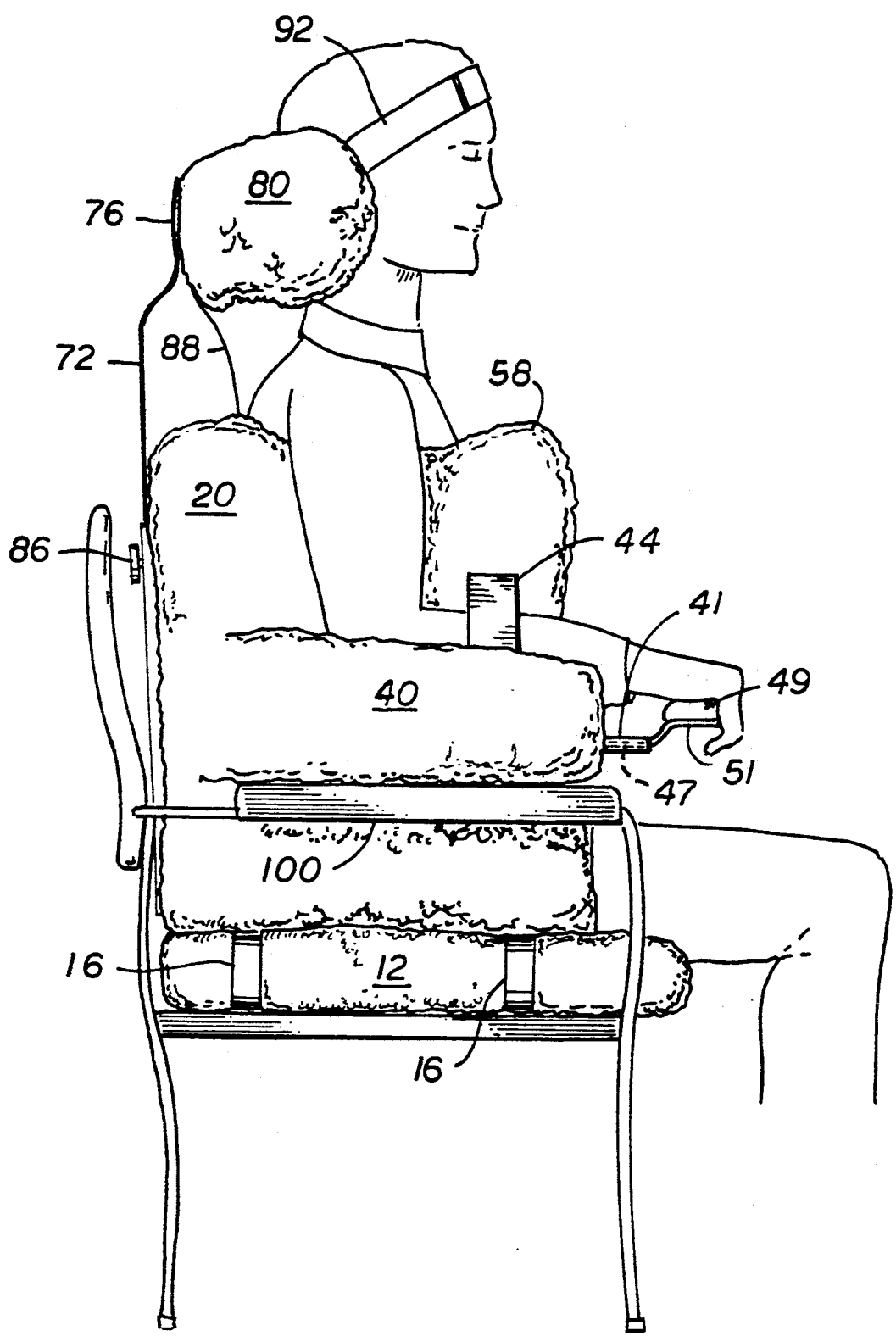
FIG. 5 is a side elevational view of the second embodiment positioned in a chair.
Figure 6:
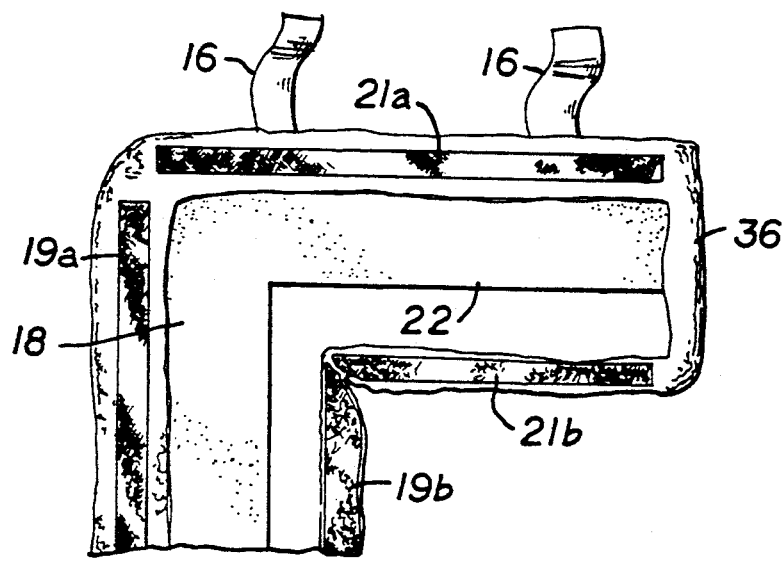
FIG. 6 is a partial bottom plan view of the rear wall and a side wall of the vest, showing how flaps are formed therein to admit the foam core of the device into the cover therefore.
Figure 7:
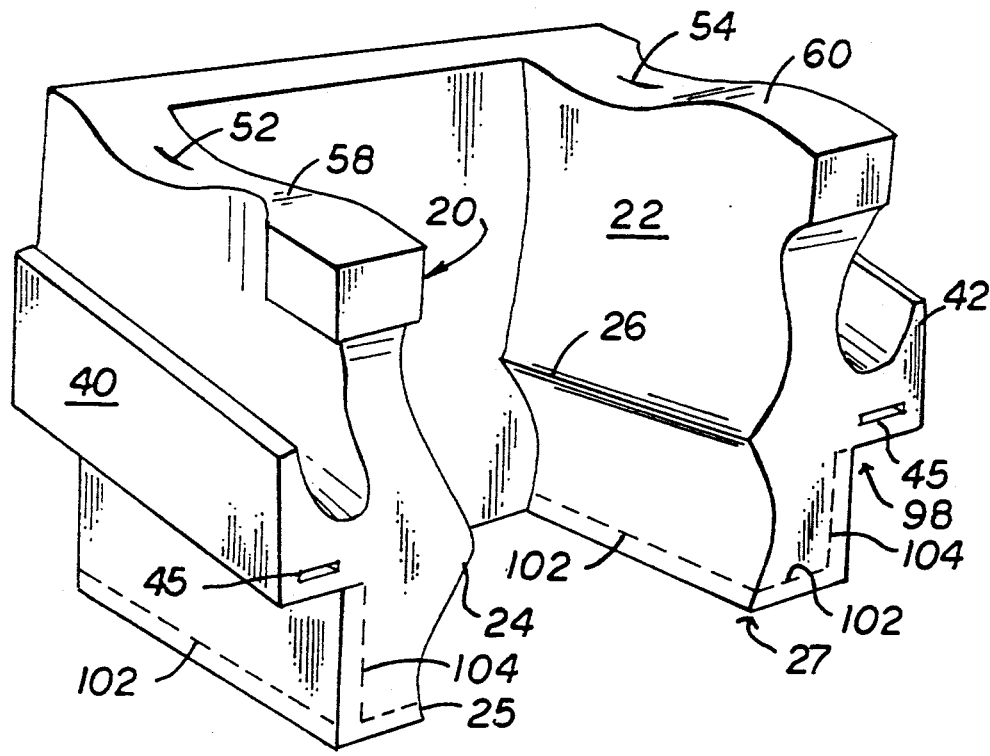
FIG. 7 is a perspective view of the core structure that underlies the cover of both embodiments.

It should be understood from the outset that all of the walls are made of a suitable foam or sponge-like material that has sufficient rigidity to hold its shape and to affect the position of the patient's body but sufficient yieldability and resilience to avoid causing discomfort to the patient undergoing treatment. It should also be understood that the device relies upon the firmness of the chair upon which it is positioned to provide a strong foundation. It should further be understood that all walls are preferably covered by a thick layer of natural or synthetic fleece. In FIGS. 1-5, the underlying walls are not shown, but they are shown in FIGS. 6 and 7. To simplify this description, the walls are referred to as rear walls and side walls without distinction between the underlying walls made of a foamed material and the overlying fleece cover therefore, and the same reference numerals are applied to both the fleece and the foam walls.

The inner surface of each side wall 20, 22 has an inwardly-projecting, longitudinally-extending bulge or protuberance 24, 26 integrally formed therewith. As should be clear from FIGS. 1 and 2, those protuberances will bear against the sides of an individual seated atop cushion 12, precisely at the waist line of the individual, if side walls 20, 22 are brought towards one another as indicated by directional arrows 28 in FIG. 1. Bulges 24, 26 appear to be rounded, as is desirable, in FIGS. 1 and 2, because of the thickness of the fleece cover; FIG. 7 discloses the shape of the bulges as formed in the underlying side walls 20 and 22, respectively.

Additional bulges are provided at the lowermost end of each side wall and are denoted 25, 27 in FIG. 7, where they are best shown; they help center the patient's pelvic region and assist in holding the pelvic region against lateral shifting.

Figure 2:
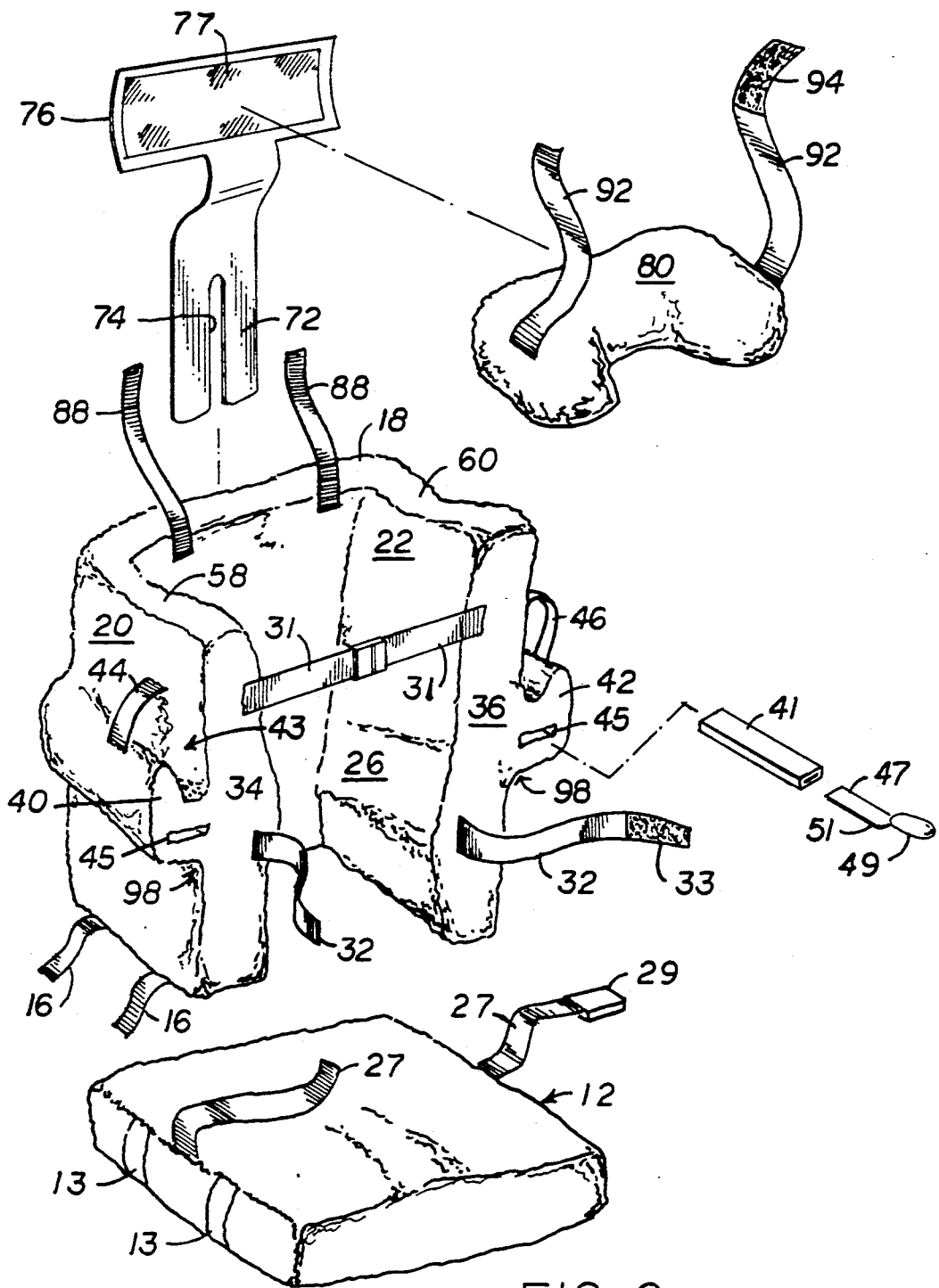
FIG. 2 is an exploded perspective view of a second embodiment.

Lap strap 27, shown in FIGS. 1 and 2, is anchored at its opposite ends to cushion 12, about mid-depth thereof. It works with hip bulges 25, 27 to further secure the pelvic region of the patient against lateral displacement or other unwanted movement. It includes a padded member 29 that cushions the area of the patient's body where the free ends of the opposing strap members are releasably connected to one another.

A belt member 30 is depicted in FIG. 1; it circumscribes vest 10 and is held in place just below the upper edge thereof by a plurality of circumferentially spaced belt loop members that are not visible in FIG. 1. The belt overlies the patient's chest and forces the spine of the patient into extension. The opposite ends of belt 30 are covered with complemental hook and loop fastening means and said opposite ends are detachably securable to one another at the front of vest 10, as depicted in FIG. 1, in an infinite plurality of positions of functional adjustment. In the claims that follow, belt 30 is referred to as a side wall positioning means for converging the side walls toward one another.

Strap members 32 are fixedly secured as depicted in FIGS. 1 and 2 to a front edge 34, 36 of side walls 20, 22, respectively, at a point on said front edges substantially coincident with the bulges 24, 26. Thus, bulges 24, 26 and straps 32 are about the same distance above the plane of seat cushion 12; as mentioned earlier, they are coincident with the patient's waistline. In the claims that follow, straps 32 are referred to as waistline straps. The respective distal free ends 33 (FIG. 2) of straps 32 are covered with complemental hook and loop-type fastening means so that bulges 24, 26 can be brought toward one another and held at any preselected position by the simple expedient of increasing the amount of overlap of straps 32 with one another. The hook and loop-type fastening means, theoretically, could cover all of straps 32 so that bulges 24, 26 could be brought very close together as may be needed for treatment of an infant.

In the embodiment of FIG. 2, belt 30 and its loops are eliminated in favor of straps 31, 31 which have the same construction as straps 32 and which perform the same function as belt 30. Straps 31 may have their anchored ends fixedly secured to forward edge walls 34, 36 as depicted or to respective exterior surfaces of side walls 20, 22. In the claims, straps 31, 31, like belt 30, are referred to as side wall positioning means to distinguish them from the waistline straps 32, 32.

When side walls 20, 22 are brought progressively closer together, bulges 24, 26 are also brought closer together, of course. Thus, belt 30 or straps 31, at least to some extent, and straps 32 particularly enable the health care professional to urge bulges 24, 26 against the sides of the patient, at the waistline, with as little or much pressure as may be required.

If the built-in bulges 24, 26 are inadequate to accomplish the spinal or other realignment needed for a particular patient, one or more supplemental bulge-providing means or bolster pads 38 (upper left corner of FIG. 1) may be employed. One or more of said pads may be slipped between the fleece cover and the appropriate foamed rear or side wall as needed; a plurality of such bolster pads may be employed, and they may have differing sizes and shapes and may be placed at differing positions throughout the device, in view of the novel foam core and fleece cover construction that enables the selective addition of supplemental bolster pads such as pad 38.

Armrests 40, 42 are integrally formed with each side wall 20, 22, on the exterior side thereof; they perform the function their name implies. Each armrest defines a concavity 43 that receives the patient's forearm, and straps 44, 46 are provided to hold the patient's forearm within each armrest. Hook and loop-type fasteners are provided on straps 44, 46 to facilitate their quick closing and opening; they form a loop as depicted in FIG. 2 when properly closed about a patient's forearm.

The novel extension assembly that complements each armrest 40 and 42 is denoted 39 as a whole in FIGS. 1 and 2; it includes a housing 41 of parallelepiped construction that is received and fixedly secured within blind slot 45 formed in each armrest 40, 42. Housing 41 telescopically receives base 47 of the arm rest extension, and a therapeutically designed hand support member 49 is detachably secured to the distal end of each base by suitable fastening means 51 (FIG. 2). Thus, multiple hand support members of differing designs may be employed to accommodate patients of differing needs, and the telescopic mounting of base 47 accommodates patients of all sizes.

Although side walls 20, 22 have some rigidity, the health care professional may at times desire increased rigidity in said side walls to better treat a patient. The increased rigidity is provided by a flat, elongate stay member 50 (upper right corner of FIG. 1); it is selectively insertable into a blind slot 52 or 54 formed in side walls 20, 22, respectively, as indicated by broken line 56 in FIG. 1 more particularly, blind slots 52, 54 are formed in the dished—to comfortably accommodate the patient's armpits—respective upper edges 58, 60 of side walls 20, 22, and extend downwardly into said side walls a distance substantially equal to the length of rigid stay member 50. Since use of two stays 50 at one time is contraindicated, only one stay 50 is provided. The dished upper end of each side wall is perhaps best depicted in FIG. 7. Due to the thickness of the side walls and the fleece that covers them, the patient's arms and shoulders are therapeutically abducted when the patient sits in the novel appliance as depicted in FIG. 5.

Figure 3:
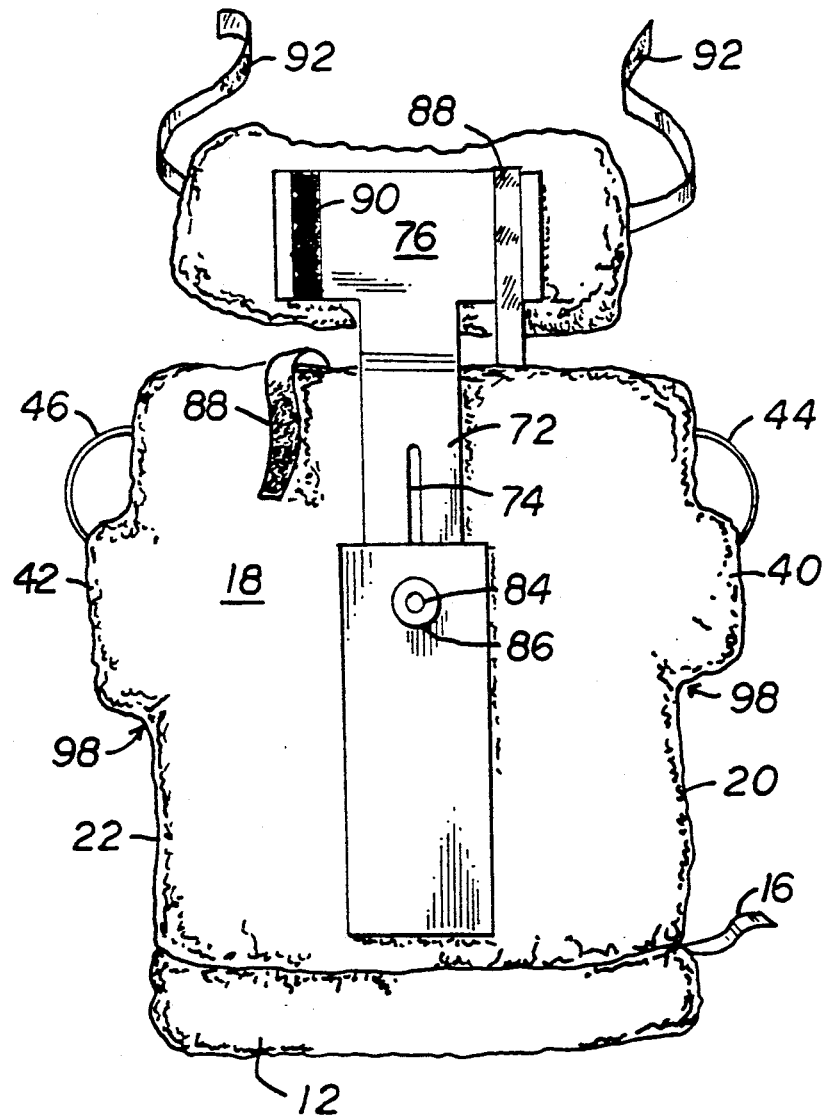
FIG. 3 is a rear elevational view of the second embodiment.
Figure 4:
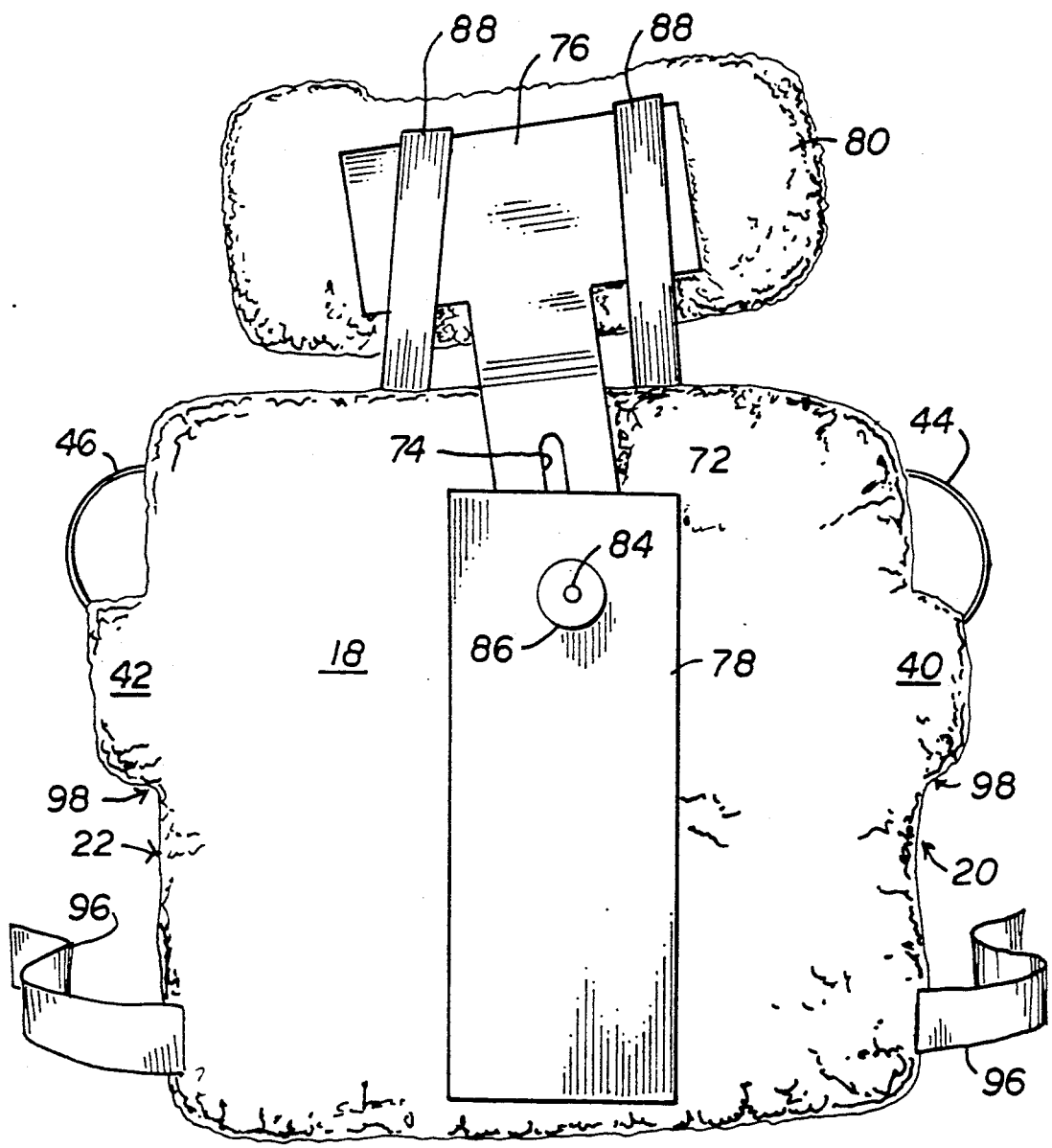
FIG. 4 is a rear elevational view of the second embodiment when the head rest is tilted with respect to horizontal.

Head rest 70, as best understood in connection with FIGS. 2-4, includes a flat, linear-in-configuration leg member 72 that is longitudinally slotted as at 74 and which is surmounted by a trough-shaped base member 76; a forward surface of member 76 is covered with hook and loop-type fastening members 77 as depicted in FIG. 2 and detachably engages a cushioned and suitably contoured head-cradling member 80 that is made of a material engageable by hook and loop-type fasterers; accordingly, the position of cradling member 80 with respect to base 76 is easily adjustable.

Leg member 72 is slidably received within a vertically oriented pocket member 78, formed of leather or other suitable material, that is secured to the outer surface of back wall 18. An aperture is formed in pocket member 78 to receive screw member 84 that has an enlarged head 86 to facilitate hand tightening thereof. Thus, vertical adjustment of the head rest assembly is accomplished by moving leg 72 up or down as needed with screw member 84 loosened and tightening said screw member when the desired vertical adjustment is achieved.

A pair of strap members 88 are provided to enable the health care professional to further adjust the position of the head rest assembly. Each strap 88 has one end fixedly secured to back wall 18 of vest 10 and hook and loop-type fastener means are provided on the free end of each strap 88. Complemental strips 90 of hook and loop-type fastener means are provided on opposite ends of base 76 to releasably engage said straps; only one of said strips 90 is visible in FIG. 3. Accordingly, by selectively increasing or decreasing the overlap of the respective hook and loop-type fastener means on the straps 88 and strips 90, the head rest assembly can be tilted at differing angles from the horizontal as depicted in FIG. 4.

Each strap member of straps 92 has a first end fixedly secured to opposite ends of cradling member 80 as shown in FIGS. 2 and 3; one of said straps is preferably made of a material that is engageable by hook and loop-type fastening means and a second strap member has a distal free end thereof covered with a complemental hook and loop-type fastening means as indicated in FIG. 2 by the reference numeral 94. This enables said straps to be detachably securable to one another with any preselected degree of tightness over a patient's forehead as depicted in FIG. 5. All detachable strap members of this disclosure are preferably of similar construction.

Hook and loop-type fasteners are also employed in the manner depicted in FIG. 6. To facilitate insertion and removal of the foam back and side walls from the fleece cover, the bottom edge of the cover is slit to form opposing flaps and said flaps are provided with suitable hook and loop-type fastening means to facilitate their opening and closing. More particularly, opposing strips of hook and loop fastening means 21a, 21b are fixedly secured to the opposing flaps of side wall 22 of the fleece cover so that when strip 21a is brought into overlying relation to strip 21b, or vice versa, foam sidewall 22 is covered along its lowermost edge. Similarly, the lowermost edge of fleece back wall 18 is closed over foam back wall 18 by bringing together fastening strips 19a and 19b. FIG. 6 shows the fleece cover in its open configuration, thereby exposing to view foam back 18 and side wall 22 and the just-mentioned fastening strips that are sewed to the inside of the opposing flaps of the fleece cover.

Vest 10 may be tied to a conventional chair or to a wheelchair by elongate straps 96 (FIG. 4). Each strap 96 has a first end fixedly secured to back wall 18; the two straps wrap around the wheel chair or other object to which vest 10 is to be secured and the opposite ends thereof are secured together by any suitable means.

The novel apparatus 10 is precisely formed to fit any conventional chair having side arms. Note in almost all of the Figs. that an overhang 98 is formed where each armrest projects outward from its associated side wall. Each overhang 98 receives an arm 100 of a chair as is shown in FIG. 5; it is the chair and its arms that provide a major part of the structural rigidity of the novel apparatus 10.

The dotted lines 102 appearing near the top and bottom edges of side walls 20, 22 in FIG. 1 represent razor-cuttable lines; the foam part of the vest is removed from its cover and a suitable cutting means is employed to shorten the height of said side walls as may be needed for the comfort and appropriate fit of children or small adults by shaving said side walls along said lines as needed. The cover is then replaced, of course. Similar razor lines 104 are shown in FIG. 7; they facilitate narrowing of the appliance 10 by shaving off excess foam in the lower side wall areas thereof as may be needed to conform appliance 10 to a particular chair.

The versatility of the novel device is thus seen to far surpass that of earlier medical appliances having utility in the field of this invention.

This invention is clearly new and useful. Moreover, it was not obvious to those of ordinary skill in this art at the time it was made, in view of the prior art when considered as a whole in accordance with the requirements of law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, What is claimed is:

1. A medical appliance, comprising:
   a seat cushion;
   a vest member detachably securable to said seat cushion;
   said vest member including a transversely disposed, upstanding back wall and a pair of laterally spaced apart, longitudinally disposed, upstanding side walls projecting forwardly with respect to said back wall; and
   side wall positioning means for converging said side walls toward one another and for holding said side walls in a converged position;
   whereby appropriate adjustment of said first side wall positioning means affords treatment of a spinal deformity of a patient seated on said seat cushion.

2. The appliance of claim 1, wherein said side wall positioning means is an adjustable-length belt member that circumscribes said back and side wall.

3. The appliance of claim 1, wherein said side wall positioning means includes a pair of straps, each of said straps having an outer end thereof fixedly secured to a side wall of said vest and an inner end releasably and adjustably securable to the inner end of its opposing strap.

4. The appliance of claim 1, wherein each of said side walls is formed of a foam material and has an outer side and an inner side, wherein a longitudinally extending armrest is integrally formed on each of said side wall outer sides at a common, preselected spacing above said seat cushion, and wherein each armrest defines an overhang area that receives the arms of a chair that supports the appliance.

5. The appliance of claim 1, wherein each of said side walls has a flat bottom edge disposed in abutting relation to said seat cushion, wherein each of said side walls has a top edge that is dished to accommodate a patient's armpits, wherein an upstanding blind slot is formed in each of said side walls, and further comprising a rigid stay member adapted to slidably fit within each of said blind slots, whereby a side wall having a stay member disposed within a blind slot is made more rigid than its opposing side wall, said stay member thereby providing an additional treatment tool for use by a therapist.

6. The appliance of claim 1, wherein said back wall has a flat bottom edge disposed in abutting relation to said seat cushion, and further comprising a pocket member secured to an exterior side of said back wall, substantially centrally thereof, and further comprising a head support means, said head support means having a leg member slidably disposed in said pocket member and having a base that surmounts said leg member.

7. The appliance of claim 6, further comprising a pair of head support-engaging strap members, each of which has a first end fixedly secured to said back wall and each of which has a second, free end releasably and adjustably securable to said base at opposite ends thereof so that the position of the base is adjustable through adjusting the respective lengths of said head support-engaging strap members.

8. The appliance of claim 7, wherein said base has a trough-like shape and a forward side at least partially covered with a hook and loop-type fastening means, and further comprising a cushioned and suitably contoured head-cradling member detachably securable to said forward side of said base.

9. The appliance of claim 1, further comprising a cover for said seat, back wall, and side walls, said cover being formed of a material that is soft and that breathes well so that it transfers a patient's body heat away from the patient.

10. The appliance of claim 1, wherein said back and side walls are releasably secured to said seat cushion by a plurality of fasteners of the hook and loop type.

11. The appliance of claim 1, further comprising an arm rest strap member for holding down a patient's forearm, each of said armrests having an armrest strap member associated therewith, and each of said armrests having a concavity formed in an upper surface thereof to accommodate a patient's forearm.

12. The appliance of claim 4, further comprising a waistline positioning means for converging said side walls toward one another and for holding said side walls in said converged position, said waistline positioning means including a pair of strap members secured to said side walls, each strap member of said pair of strap members having a free end releasably securable to a free end of its opposing strap member, and said waistline positioning means being disposed downwardly of said side wall positioning means.

13. The appliance of claim 12, wherein each side wall has an inner side and an outer side, wherein an inwardly extending, longitudinally extending protuberance is formed on each inner side wall at a common, preselected spacing from said seat, and wherein the respective outer ends of said waistline strap members are secured to said side wall leading edges at a position substantially coincident with said inwardly extending protuberances so that a therapist may treat the patient by adjusting said waistline strap members and hence the position of said protuberances.

14. The appliance of claim 1, further comprising razor lines formed adjacent top and bottom edges of said side walls and near the surface of said side walls to facilitate cutting of said side walls to accommodate patients of differing heights and other physical characteristics and to narrow the appliance as needed to fit into a chair.

15. The appliance of claim 4, further comprising an extension member associated with each of said armrests to accommodate patients having forearms of differing lengths, each extension member including a housing fixedly secured within an associated armrest, a base member telescopically received within said housing, and a therapeutic hand splint means detachably secured to a free end of said base member.

16. The appliance of claim 13, further comprising a cover for covering said back wall and said side walls, said cover conforming to the shape of said armrests and said inwardly extending protuberances, said cover including a top edge wall that abuttingly engages and overlies respective top edges of said back wall and said side walls, and said cover having a bottom edge wall that opens to receive said back walls and said side walls, said bottom edge wall having complemental hook and loop type fastening material attached to opposing flaps thereof to facilitate opening and closing of said bottom edge wall.

17. A medical appliance, comprising:
a seat cushion;
a three-sided vest detachably secured to said seat cushion;
a head-supporting member adjustably mounted to said vest so that the head of an individual seated on said seat cushion is supported by said head-supporting member;
means for tightening said vest around the trunk of said individual;
a pair of armrests integral with said vest and being disposed on opposite sides thereof;
an overhang area being defined under said armrests where said armrests project from the sides of said vest, said overhang area adapted to receive arms of a chair upon which the appliance may be positioned; and
said seat cushion and vest being formed of a foamed material and being covered with a layer of material that is comfortable to a patient being treated by said appliance.

18. The appliance of claim 17, further comprising an armrest extension member telescopically mounted within each armrest, and a hand splint means secured to a distal free end of each extension member.

19. A medical appliance, comprising:
a seat cushion;
a three-sided vest detachably secured to said seat cushion;
a head-supporting member adjustably mounted to said vest so that the head of an individual seated on said seat cushion is supported by said head-supporting member;
means for tightening said vest around the trunk of said individual;
a pair of armrests integral with said vest and being disposed on opposite sides thereof;
an overhang area being defined under said armrests where said armrests project from the sides of said vest, said overhang area adapted to receive arms of a chair upon which the appliance may be positioned;
said seat cushion and vest being formed of a foamed material and being covered with a layer of material that is comfortable to a patient being treated by said appliance; and
an armrest extension member telescopically mounted within each armrest, and a hand splint means secured to a distal free end of each extension member.

20. The appliance of claim 19, wherein said three-sided vest includes a pair of transversely spaced apart side walls, and further comprising inwardly projecting protuberances formed in interior faces of said side walls, said protuberances being positioned above said seat cushion at a predetermined height so that said protuberances bear against the waistline of an individual being treated by said appliance when said vest is tightened around the trunk of the individual.

* * * * *